(12) United States Patent
Zhu

(10) Patent No.: US 6,776,520 B2
(45) Date of Patent: Aug. 17, 2004

(54) METHOD FOR DETERMINING A COEFFICIENT OF THERMAL EXPANSION AND APPARATUS THEREFOR

(75) Inventor: Han Zhu, Chandler, AZ (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 10/099,526

(22) Filed: Mar. 15, 2002

(65) Prior Publication Data

US 2002/0167988 A1 Nov. 14, 2002

Related U.S. Application Data

(60) Provisional application No. 60/276,368, filed on Mar. 16, 2001.

(51) Int. Cl.[7] .................................................. G01N 3/08
(52) U.S. Cl. .............................. 374/55; 374/46; 374/56
(58) Field of Search .......................... 374/46–50, 55–56, 374/57, 4–5, 10–12, 14, 52; 73/826, 789

(56) References Cited

U.S. PATENT DOCUMENTS

| | | | | |
|---|---|---|---|---|
| 4,019,365 A | * | 4/1977 | Woo ............................ | 73/15.6 |
| 4,354,764 A | * | 10/1982 | Achermann et al. .......... | 374/56 |
| 4,924,477 A | * | 5/1990 | Gilmore et al. ............... | 374/55 |
| 5,370,457 A | * | 12/1994 | Iizuka ......................... | 374/51 |
| 5,390,127 A | * | 2/1995 | Tang et al. .................. | 364/472 |
| 6,009,378 A | * | 12/1999 | Tang et al. .................... | 702/34 |
| 6,200,022 B1 | * | 3/2001 | Hammiche et al. ........... | 374/46 |
| 2002/0136262 A1 | * | 9/2002 | Feger .......................... | 374/55 |

OTHER PUBLICATIONS

Zhu, H., Guo, Y., Li, W., and Tseng, A.A., "Mechanical Characterization of Solder Mask Materials in Electronic Packaging Applications," *The Seventh Intersociety Conference on Thermal and Thermomechnical Phenomena in Electronic Systems*, Las Vegas, NV, USA, May, 2000.

Qian, Z., Lu, M., Ren, W., and Liu, S., "Fatigue Life Prediction of Flip–Chips in Terms of Nonlinear Behaviors of Solder and Underfill," *Proceedings of the 49th Electronic Components and Technology Conference (ECTC)*, San Diego, CA, 1999.

Yu, Q., and Shiratori, M., "Fatigue–Strength Prediction of Microelectronics Solder Joints Under Thermal Cycling Loading," *IEEE Transactions on Components, Packaging, and Manufacturing Technology Part A*, vol. 20, No. 3, 1997.

Darveaux, R., Norton, L., and Carney, F., (1995), "Temperature Dependent Mechanical Behavior of Plastic Packaging Materials," § *Proceedings—Electronic Components and Technology Conference*, May 21–24, IEEE pp. 1054–1058 0569–5503.

Michaelides, S., and Sitaraman, S.K., (1998) "Effect of Materials and Geometry Parameters on the Thermo–Mechanical Reliability of Flip–Chip Assemblies" § *Thermo–Mechanical Phenomena in Electronic Systems Proceedings of the Intersociety Conference*, EIOA IEEE pp. 193–200.

Schmitt, G.P., Appelt, B.K., and Gatro, J.T., (1989) "Polymers and Polymer–based Composites for Electronic Applications," Chapter 11, *Principles of Electronic Packaging*, McGraw Hill.

Ume, I.C., Martin, C., and Gatro, J.T. (1997) "Finite Element Analysis of PWB Warpage due to the Solder Masking Process," *IEEE Transactions on Components, Packaging, and Manufacturing Technology, Part A*, v 20, n 3, IEEE pp. 295–306 1070–9886.

* cited by examiner

*Primary Examiner*—Gail Verbitsky
(74) *Attorney, Agent, or Firm*—Gallagher & Kennedy, P.A.; Thomas D. MacBlain

(57) ABSTRACT

A method for determining the Coefficient of Thermal Expansion of a specimen. The specimen is placed in the tester and a tensile force is applied to the specimen. The specimen is equilibrated at a first temperature and then elongated. After reaching a desired elongation, the specimen is equilibrated at another temperature. The tensile force on the specimen is changed to a predetermined value or until the specimen fails. A force-displacement curve is generated from the stressed specimen. The force-displacement curve is converted into a stress-strain response, from which the Coefficient of Thermal Expansion is determined.

3 Claims, 3 Drawing Sheets

US 6,776,520 B2

METHOD FOR DETERMINING A COEFFICIENT OF THERMAL EXPANSION AND APPARATUS THEREFOR

The present patent application claims priority from U.S. Provisional Patent Application Ser. No. 60/276,368 filed Mar. 16, 2001.

FIELD OF THE INVENTION

This invention relates, in general, to the coefficient of thermal expansion and, more particularly, to a method for determining the coefficient of thermal expansion.

BACKGROUND OF THE INVENTION

Matter, hence material, has thermal properties that should be considered when being used to manufacture articles or workpieces. It is important to give serious thought to the thermal conductivity of a material in industries such as the semiconductor industry, the transportation industry, the construction industry, and the garment industry to name a few. For example, in the semiconductor industry it is important to design semiconductor devices to propagate heat away from their junction regions so they don't undergo a catastrophic thermal failure during operation. Another important thermal property of a material that should be evaluated is the Coefficient of Thermal Expansion (CTE). Still referring to the semiconductor device example, if the semiconductor device includes two thin film materials adjacent to one another and these materials have drastically different Coefficients of Thermal Expansion (CTE's), the semiconductor device could suffer a catastrophic thermal failure as the device is heated. The failure occurs because one of the two materials expands at a much quicker rate than the other material, thereby creating stresses in both materials which damage one or both of them.

One technique for characterizing the CTE of a material is based on a free body expansion mechanism in which the increase or decrease in volume of the material is proportional to the temperature change. The change in volume of the material caused by the change in temperature is measured using an instrument called a Thermal Mechanical Analyzer (TMA). The volume change is then converted to a CTE value. This technique is used in the "Standard Test Method for Linear Thermal Expansion of Solid Materials by Thermomechanical Analysis." This standard is set forth in ASTM E831-2000. Another technique for characterizing the CTE of a material employs electric resistance strain gages, where a strain gage is bonded to the material to gauge the thermal deformation of the material. This technique is used in the "Standard Test Method for Linear Thermal Expansion of Rock Using Bonded Electric Resistance Strain Gages." This standard is set forth in ASTM D5335-1999. In both of these techniques, the CTE's are measured under unstressed conditions.

Accordingly, a need exists for a method and an apparatus for measuring the CTE's of materials under stressed conditions.

SUMMARY OF THE INVENTION

The present invention satisfies the foregoing need by providing a method for determining the coefficient of thermal expansion for a specimen. In accordance with an embodiment of the present invention, a specimen or material is equilibrated at a first temperature. A first stress is imparted on the material and then the temperature is changed to a second temperature. The material is equilibrated at the second temperature and a second stress is imparted on the material. The stress change of the material is determined and used to calculate the coefficient of thermal expansion of the material.

BRIEF DESCRIPTION OF THE DRAWING

The present invention will be better understood from a reading of the following detailed description, taken in conjunction with the accompanying drawing figures in which like references designate like elements and in which.

DETAILED DESCRIPTION

The present invention provides a method and an apparatus for measuring the CTE of a material in a stressed state or condition. One aspect of this invention is that the material or specimen is stressed while undergoing a temperature change. Typical specimens include thin films, fibers, etc. Another aspect of this invention is that the material or specimen is small, i.e., at least one characteristic dimension of the specimen can be on the order of millimeters or sub-millimeters such as, for example, microns. Yet another aspect of this invention is that when specimens are under stress, the CTE values of the specimen are related to the stress change resulting from the change in temperature. The stress change can be a stress drop or a stress increase.

Figure 1:
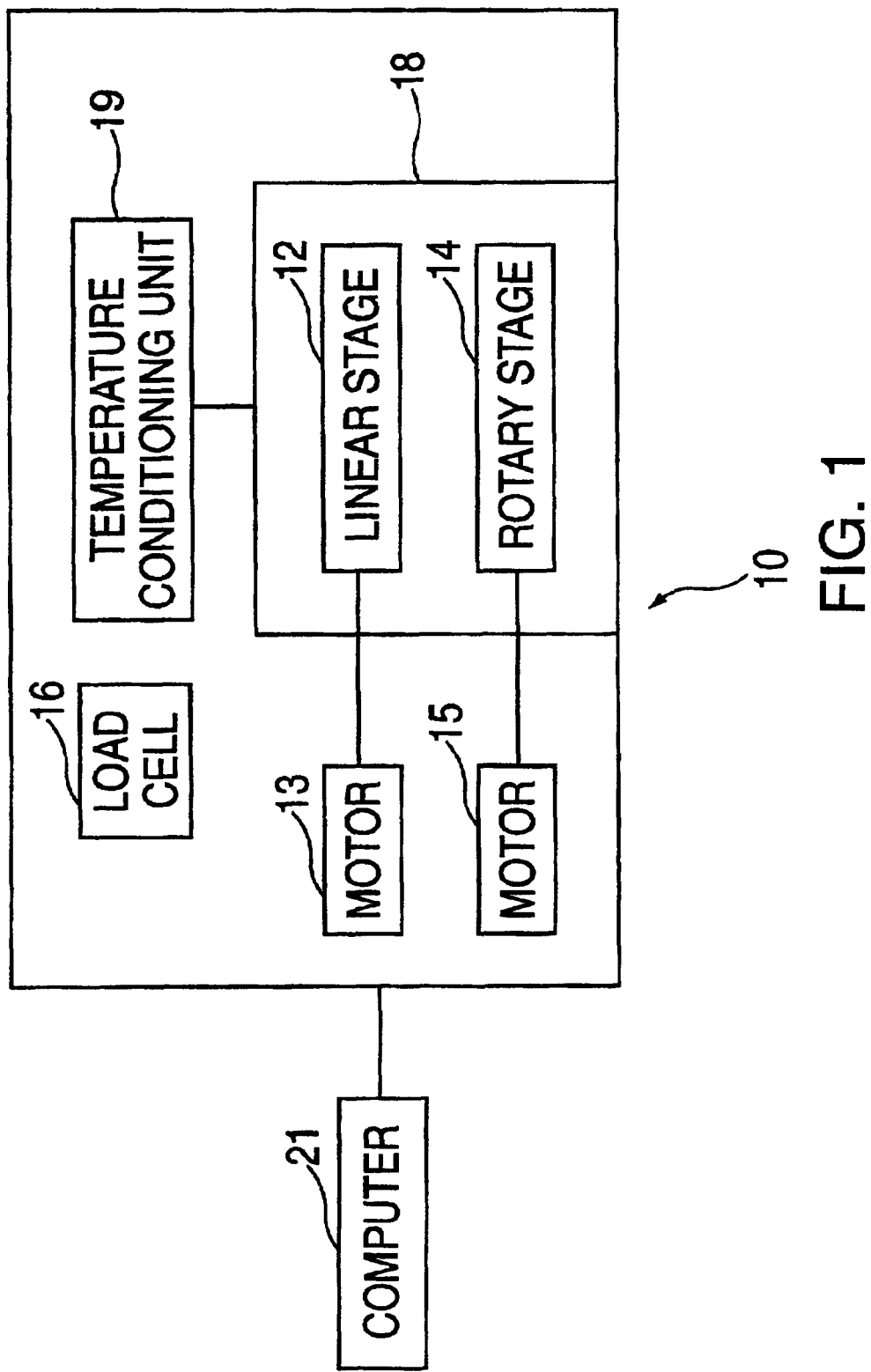
FIG. 1 is a schematic block diagram of a tester in accordance with an embodiment of the present invention.

FIG. 1 is a schematic block diagram of a tester 10 for measuring the coefficient of thermal expansion of a material in accordance with an embodiment of the present invention. Tester 10 is a micro thermo-mechanical two-axis tester having a linear stage 12, a rotary stage 14, a six-axis load cell 16, and a small environmental chamber 18. Linear stage 12 and rotary stage 14 are positioned within environmental chamber 18 and coupled to a linear motor 13 and a DC rotary motor 15, respectively. Load cell 16 is operatively coupled to motors 13 and 14. A temperature conditioning unit 19 capable of regulating the temperature within environmental chamber 18 between −100 degrees Celsius (°C.) and 300° C., inclusive, is coupled to environmental chamber 18. Tester 10 further includes a computer 21 is coupled to tester. Computer 21 controls tester 10 as well as processes data, i.e., manipulates the data. Although computer 21 is described as being part of tester 10, it should be understood that computer 21 may be separate from tester 10.

Preferably, tester 10 has a high load and displacement resolution, e.g., 2 grams in force and 0.1 micron in length, respectively, and is capable of providing a tensile and compressive load of up to 20 kilograms (kg) and a torsional load of up to 20 Newton-meters (N-m). Moreover, it is preferable that the maximum translational range that tester 10 can apply to a sample is 100 millimeters (mm), the maximum rotational range is 360°, and the translation speed can vary from 0.0005 millimeters per second (mm/s) to 10 mm/s. Temperature conditioning unit 19 uses liquid nitrogen to cool the ambient within environmental chamber 18 to its lowest temperature, e.g., −100° C., and heating elements to heat the ambient within environmental chamber 18. In addition, tester 10 is capable of operating in two loading modes: the uniaxial mode and the torsion mode and has four loading configurations available: static, fatigue, creep, and relaxation. Control of the tester and the data manipulation is fully computerized.

Figure 2:
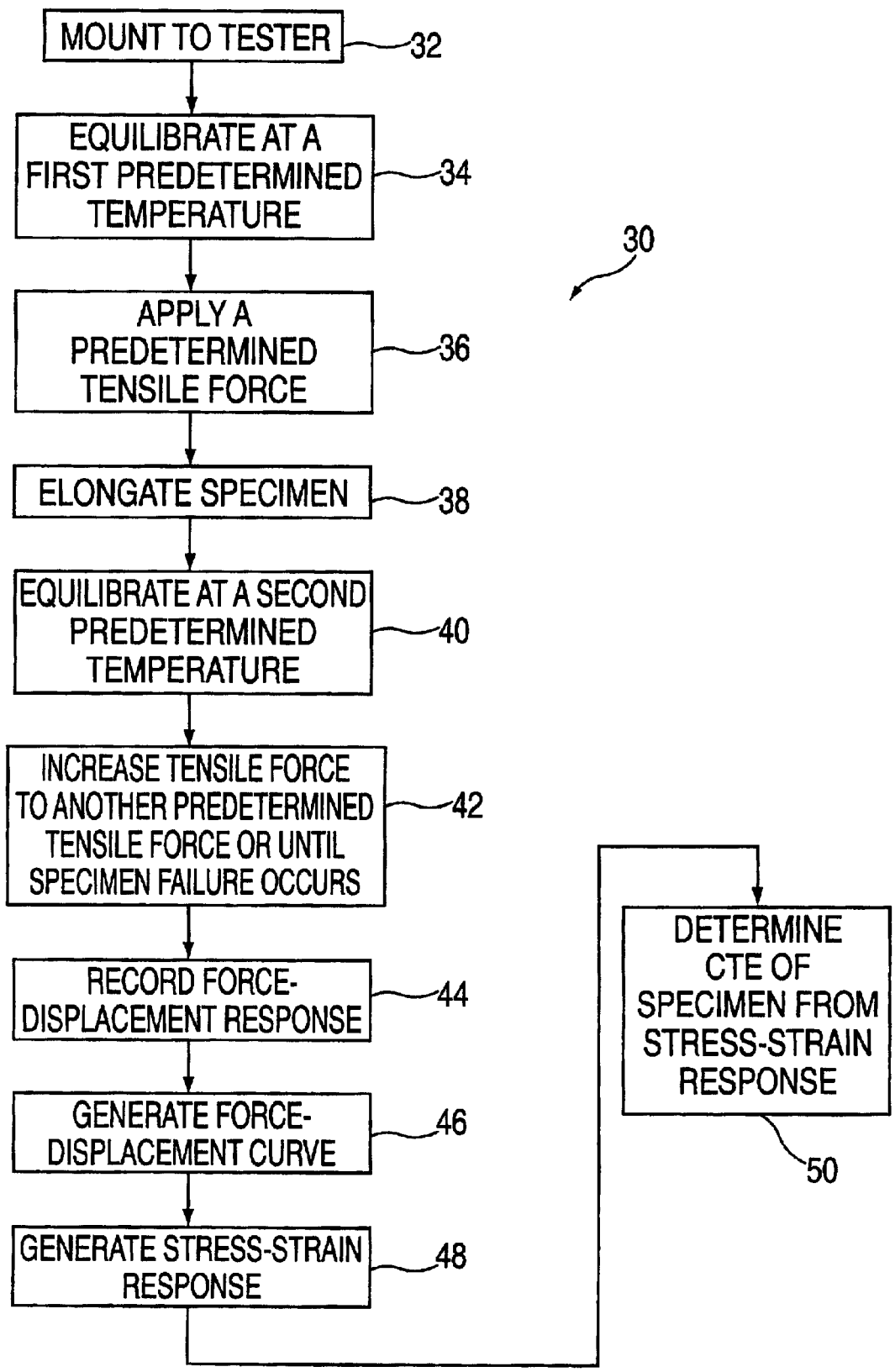
FIG. 2 is a flow chart of a method for determining the Coefficient of Thermal Expansion of a material in accordance with an embodiment of the present invention.

FIG. 2 is a flow chart 30 of a method for determining the CTE of a sample in accordance with an embodiment of the present invention. In a beginning step, a sample or specimen of a material is mounted to a tester such as, for example, tester 10 (reference number 32). The specimen is placed in environmental chamber 18 and equilibrated at a temperature $T_1$ (reference number 34). Computer 21 is programmed so that tester 10 applies a tensile force or load level of a predetermined value to the specimen (reference number 36). By way of example, temperature $T_1$, is room temperature, e.g., 25° C. and the tensile force is XX. It should be noted that the order of the steps described by reference numbers 34 and 36 is not a limitation of the present invention. For example, the tensile force may be applied to the specimen before or during temperature equilibration.

After achieving temperature equilibration, computer 21 activates tester 10 to elongate the specimen at a predetermined rate, e.g., 0.5 micron per second. The elongation continues until the elongated specimen has the desired tensile force on it (reference number 38).

Because the force level is preset, tester 10 stops elongating the specimen when load cell 16 detects a load that meets the specified force magnitude. Preferably, computer system 21 records and displays the force displacement response of the specimen.

The temperature in environmental chamber 18 is changed from temperature $T_1$ to a different temperature, $T_2$, and maintained at temperature $T_2$ for a time period that allows the specimen to reach thermal equilibrium (reference number 40). After the specimen has equilibrated at temperature $T_2$, the tensile force applied to the specimen is increased to a predetermined value or until the specimen fails (reference number 42). The force displacement response is recorded on for example, computer 21, as the tensile strength is increased (reference number 44). It should be understood that the means for recording force displacement response is not a limitation of the present invention. For example, a chart recorder may be used to record the force displacement response.

Figure 3:
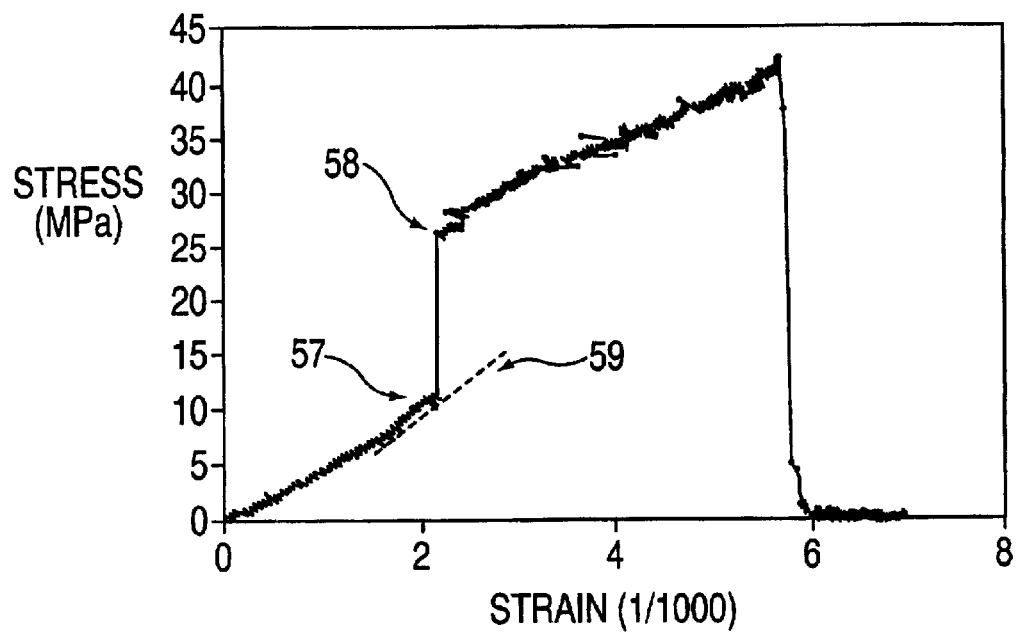
FIG. 3 is a stress-strain response generated in accordance with the method of FIG. 2.

When the tensile force on the specimen is increased, a stress change is observed. If the temperature change is in a negative direction, i.e., $T_2$ is less than temperature $T_1$, the stress change is in a positive direction, i.e., the stress increases. Conversely, if the temperature change is in a negative direction, i.e., $T_2$ is greater than temperature $T_1$, the stress change is in a negative direction, i.e., the stress decreases. After completing the testing procedure, a force displacement curve is generated (reference number 46). Referring now to FIG. 3, the force-displacement curve is modified by incorporating the size of the specimen into the force-displacement curve to generate a stress-strain response 56 (reference number 48 of FIG. 2). Referring again to FIG. 2, the CTE of the specimen is determined using stress-strain response 56 and equations 1–7 provided hereinbelow (reference number 50).

The value of the CTE for the stressed specimen is determined using a stress jump, $\Delta\sigma$, which is determined from stress-strain response 56 of FIG. 3. In stress-strain response 56, there is a stress increase, i.e., a stress jump, that corresponds to the temperature change. The stress jump or change is typically denoted as $\Delta\sigma$ and is given by $\sigma2-\sigma1$, where $\sigma1$ and $\sigma2$ are the stress magnitudes at points 57 and 58 of FIG. 3, respectively. The relationship between the stress jump, $\Delta\sigma$, and the CTE is derived using the linear theory of thermal elasticity, which states that the stress-strain relation in describing a specimen's thermo-mechanical behavior, including the thermal strain effect, is given by:

$$\sigma = E(\epsilon - \epsilon_{th}), \epsilon_{th} = \alpha(T - T0) \quad (1)$$

where $\sigma$ and $\epsilon$ are the stress and strain, respectively, E is Young's modulus, $\epsilon_{th}$ is the thermal strain, $\alpha$ is the linear coefficient of thermal expansion, T is the current temperature, and T0 is a reference temperature at which the material has zero residual stress. It should be understood that $\alpha$ and CTE are used interchangeably. Young's modulus, E, can be determined graphically from FIG. 3 using tangent line 59 at point 51 of the stress strain curve 56, where Young's Modulus is the tangential ratio to the stress strain curve. Since the stress-strain curve is not linear, the value of Young's modulus, E, varies.

The differential form of Eq. 1 is given by:

$$d\sigma = Ed\epsilon - Ed\epsilon_{th} \quad (2)$$

Since the mechanical strain $\epsilon$ is zero during the time period when the temperature is changing, the following equation is obtained:

$$d\sigma = -E(T-T_0)d\alpha - E\alpha dT \quad (3)$$

As stated hereinbefore, $\Delta\sigma$ is the stress jump, i.e., $\Delta\sigma2-\Delta\sigma1$, where $\sigma1$ or $\sigma2$ are the stress magnitudes at points 57 and 58, respectively (see FIG. 3). The stress jump, $\Delta\sigma$, can be expressed by $$\Delta\sigma = \int_{T1}^{T2} d\sigma = \int_{T1}^{T2} -E(T-T_0)d\alpha - \int_{T1}^{T2} E\alpha dT \quad (4)$$

Eq. 4 can be simplified by assuming certain conditions apply. In a first case eq. 4 is simplified by assuming that E and $\alpha$ remain unchanged. In a second case eq. 4 is simplified by assuming that only $\alpha$ remains unchanged. In a third case eq. 4 is simplified by assuming that $\alpha$ varies linearly with temperature over the temperature range of interest.

In the first case, E and $\alpha$ are assumed to remain unchanged over the temperature range T1 to T2, [T1, T2], the CTE, i.e., $\alpha$, is given by:

$$\alpha = \frac{-\Delta\sigma}{E\Delta T} \quad (5)$$

where $\Delta T$ is T2–T1.

In the second case, only $\alpha$ is assumed to remain unchanged over the temperature range [T1, T2] and if the dependence of Young's modulus, E, on temperature is assumed to be linear, the equation for CTE, i.e., $\alpha$, is given by:

$$\alpha = \frac{-2\Delta\sigma}{(E1+E2)\Delta T} \quad (6)$$

where E1 and E2 are Young's modulus at the points $\sigma=\sigma1$ and $\sigma=\sigma2$, respectively.

In the third case, $\alpha$ is assumed to vary linearly with temperature over the temperature range [T1, T2], and E remains unchanged, the corresponding equation for CTE is:

$$1.5\alpha 2 - 0.5\alpha 1 = \frac{-\Delta\sigma}{E\Delta T} \qquad (7)$$

where α1 and α2 are the coefficients of thermal expansion of the measured specimen at temperatures T1 and T2, respectively. Because α1 and α2 can not be computed by Eq. 7 alone, a spectrum of values for α based on Eq. 7 may be determined from a series of measurements on Δσ with a multiple temperature changing scheme. For example, the CTE can be measured over a first temperature range of, for example, the range between room temperature and 0° C. Then the CTE can be determined over the range from 0° C. to −25° C., the range from −25° C. to −50° C., the range from −50° C. to −75° C., etc. It should be understood the range or increments, i.e., the twenty-five degree temperature increments, and the number of increments are not limitations of the present invention.

A natural extension of the above three cases is to analyze the case when both α and E are linear functions of temperature over the range [T1, T2].

In accordance with the present invention, the temperature is changed from temperature T1 to temperature T2. In another aspect of the present invention, the time needed for the specimen to reach its temperature equilibrium is determined. Here, the following equation is employed to provide an estimate of this time:

$$0.5h = \sqrt{\beta \Delta t} \qquad (8)$$

where h is the specimen's thickness, β is the thermal diffusivity of the specimen with the units centimeters squared per second ($cm^2 s^{-1}$), and Δt is the time estimate for the specimen reach thermal equilibrium. Therefore, when values for h and β are known, Δt can be computed by using Eq. 8.

Figure 4:
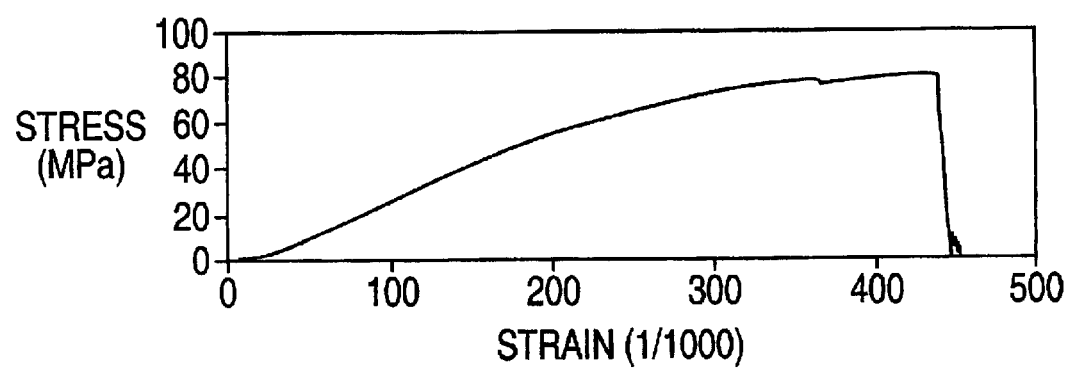
FIG. 4 is a plot of a tensile-test result in accordance with the present invention.

The curve shown in FIG. 3 is the stress-strain response for a polyimide specimen for which a temperature drop occurred when an applied stress level at about 12% of the tensile failure strength is reached. By way of example, the specimen is a thin film having a thickness of 30 microns. However, before the CTE determination can be carried out, a tensile test is performed to determine the tensile failure strength, so the information for various stress levels can be obtained for designing the follow-up temperature drop tests. The tensile test result is shown in FIG. 4.

The testing procedure for performing a temperature drop is to first stretch the specimen in tension at room temperature at a rate of, for example, 0.5 micron per second, which is extremely slow. When the load cell reaches a force level of 400 grams, which is about 12% of the failure strength at room temperature, the tester stops. At this moment, no displacement is allowed, but load cell 16 (FIG. 1) is free to register any change. Then the temperature in the environmental chamber is cooled down from room temperature to −20° C. For typical polymeric materials, β is on the order 0.0001 to 0.001. Based on Eq. 8 and using the value β=0.0001 $cm^2 s^{-1}$, the computed value for Δt is only a fraction of a second. In the test, a two minute cooling time was used. After that, the tester continues to elongate the specimen at the same rate set in the beginning until the specimen fails at −20° C. Young's modulus is determined to be 5.11 Giga Pascals (GPa) at point 57 and is 5.03 GPa at point 58 (FIG. 3). The data on stress jump due to the temperature change is recorded by computer 21. Three tests were done and their average is given in Table 1. Table 1 also includes two CTE values which correspond to the cases when the applied stress levels are at 4% and 8% of the tensile failure strength, respectively. In addition, the reported CTE value from the specimen supplier, i.e., the reported CTE value for an unstressed sample, is also listed in Table 1.

TABLE 1

Measured and Reported CTE Values

| CTE ($10^{-3}/°$ C.) | Applied stress at 4% strength level | Applied stress at 8% strength level | Applied stress at 12% strength level | Reported |
|---|---|---|---|---|
| | 0.0854 | 0.0838 | 0.0774 | 0.026 |

Although the results presented have been for the condition in which the temperature was decreased, it should be understood this is not a limitation of the present invention. More particularly, it has been shown that a stress drop occurs when the temperature of a stressed specimen is increased. Thus, the present method is suitable for determining the CTE's of specimens for which the temperature is increased or decreased.

By now it should be appreciated that a new experimental method and apparatus for measuring CTE have been provided. It can be seen from Eq. 1 that the stress change is proportional to Young's modulus. Young's modulus is usually a big number for most engineering materials. This means that the measured quantity in this method, which is the stress change (either a stress jump or a stress drop), is amplified. So a tiny change in CTE will lead to a "sizeable" change in the stress jump or stress drop. Further, the tester is of very high force resolution thereby assuring this method and apparatus provide an accurate measurement of stress.

Another advantage of the present invention is that since the specimens are small, it takes a relatively short period of time, typically a few minutes, to test them. Such a quick testing time is attractive to manufacturers. For example, testing a "regular sized" specimen may take hours or days to finish. Thus, it may be desirable to conduct micro testing on the specimen first using the method in accordance with the present invention as a screening process so that valuable time is not wasted testing regular or larger sized specimens. Since tester 10 is capable of making measurements on small specimens, the time needed for the specimens to reach thermal equilibrium after a change in temperature is short. Also, since the measurements are recorded by the tester directly and no strain gage attachment to the specimens is required, sources of error such as, for example, errors in attaching the strain gages and/or operator errors in reporting the results, are eliminated. In addition, little gripping, mounting, adjusting, and calibrating are needed when operating tester 10, which eliminates many operational errors.

It is interesting to note that, based on the results from using this method as shown in Table 1, the level of applied stress does have an affect on CTE. With all other conditions remaining the same, CTE decreases when the level of applied stress is increased. It should be understood that for some materials the CTE may increase as the stress is increased, the CTE may decrease as the stress is decreased, or the CTE may increase as the stress is decreased.

The CTE's and stress changes determined in accordance with the present invention can be used to determine other properties of a material. For example, single continuous fibers used in reinforcing composites are very small in diameter. The smallest ones can be on the order of microns. It may be possible to use the quantity of stress change described herein to back calculate the fiber diameter. This technique is also suitable for measuring the CTE's for composite materials.

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A method for determining a coefficient of thermal expansion for a material, comprising:

equilibrating the material at a first temperature;

imparting a first stress on the material by applying tension to the material;

changing the first temperature to a second temperature; equilibrating the material at the second temperature;

imparting a second stress on the material by increasing the tension on the material to a second level;

determining a stress change of the material; and using the stress change to calculate the coefficient of thermal expansion of the material by graphically determining Young's Modulus using the stress change and a tangential ratio of a stress-strain curve and determining the coefficient of thermal expansion, α, using the equation:

$$\alpha = \frac{-\Delta\sigma}{E\Delta T}$$

when Young's Modulus and the coefficient of thermal expansion remain substantially constant and where Δσ is the stress change, E is Young's Modulus, and ΔT is a temperature difference between temperatures T1 and T2.

2. A method for determining a coefficient of thermal expansion for a material, comprising:

equilibrating the material at a first temperature;

imparting a first stress on the material comprising applying tension to the changing the first temperature to a second temperature;

equilibrating the material at the second temperature;

imparting a second stress on the material comprising increasing the tension on the material to a second level;

determining a stress change of the material; and using the stress change to calculate the coefficient of thermal expansion of the material by graphically determining Young's Modulus using the stress change and a tangential ratio of a stress-strain curve and determining the coefficient of thermal expansion, α, using the equation:

$$\alpha = \frac{-2\Delta\sigma}{(E1 + E2)\Delta T}$$

when Young's Modulus is substantially linear and the coefficient of thermal expansion, a, remains substantially constant over the temperature range T1 to T2, where Δσ is the stress change, E1 and E2 are Young's Modulus at two points on a stress-strain curve, and T is a temperature difference between temperatures T1 and T2.

3. A method for determining a coefficient of thermal expansion for a material, comprising:

equilibrating the material at a first temperature;

imparting a first stress on the material comprising applying tension to the material;

changing the first temperature to a second temperature;

equilibrating the material at the second temperature;

imparting a second stress on the material comprising increasing the tension on the material to a second level;

determining a stress change of the material; and using the stress change to calculate the coefficient of thermal expansion of the material by graphically determining Young's Modulus using the stress change and a tangential ratio of a stress-strain curve and determining the coefficient of thermal expansion, α, using the equation:

$$1.5\alpha 2 - 0.5\alpha 1 = \frac{-\Delta\sigma}{E\Delta T}$$

when the coefficient of thermal expansion varies linearly with temperature over a temperature range between temperatures T1 and T2 such that α1 and α2 are the coefficients of thermal expansion at temperatures T1 and T2, where Au is the stress change, E is Young's Modulus, and ΔT is a temperature difference between temperatures T1 and T2.

* * * * *